United States Patent
Olson

Patent Number: 5,999,493
Date of Patent: *Dec. 7, 1999

[54] SYNCHRONIZATION METHOD AND APPARATUS FOR ISOLATED CLOCK SYSTEM

[75] Inventor: Kenneth F. Olson, Edina, Minn.

[73] Assignee: SurVivaLink Corporation, Minneapolis, Minn.

[*] Notice: This patent issued on a continued prosecution application filed under 37 CFR 1.53(d), and is subject to the twenty year patent term provisions of 35 U.S.C. 154(a)(2).

[21] Appl. No.: 08/649,881

[22] Filed: May 13, 1996

[51] Int. Cl.$^6$ .................................................. G04C 11/02
[52] U.S. Cl. ................................................. 368/47; 368/10
[58] Field of Search .................................. 368/47–59, 10

[56] References Cited

U.S. PATENT DOCUMENTS

| | | |
|---|---|---|
| 5,402,884 | 4/1995 | Gilman et al. . |
| 5,405,361 | 4/1995 | Persson . |
| 5,416,808 | 5/1995 | Witsaman et al. ......................... 368/47 |
| 5,461,663 | 10/1995 | Motegi ....................................... 368/47 |

OTHER PUBLICATIONS

Publication: Coordinated Universal Time—Time and Frequency Users Manual, NIST Special Publication 559.
Publication: NIST Time and Frequency Services—Article from the Time and Frequency Division NIST, Boulder, CO.
Publication: What Time Is It?—Article reprinted from the Internet, Apr. 1, 1996.
Publication: Evolution of Time Measurement—Article from the Time and Frequency Division NIST, Boulder, CO.

*Primary Examiner*—Bernard Roskoski
*Attorney, Agent, or Firm*—Patterson & Keough, P.A.

[57] ABSTRACT

A system for automatically synchronizing, isolated clocks is disclosed. In the preferred embodiment, the internal clock of an automated external defibrillator (AED) or an external defibrillator (ED) is integrated with a radio broadcast to receive standard time. The system may also include a mechanism for synchronizing the clock or a computer tracking the time of emergency calls such as 911. Further, the system enables synchronization between the AED or ED internal clock and the 911 clock such that response times can be accurately determined.

12 Claims, 4 Drawing Sheets

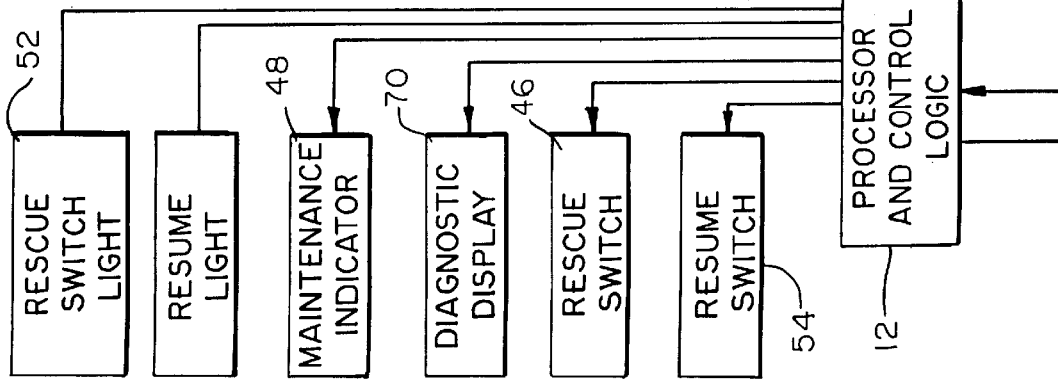

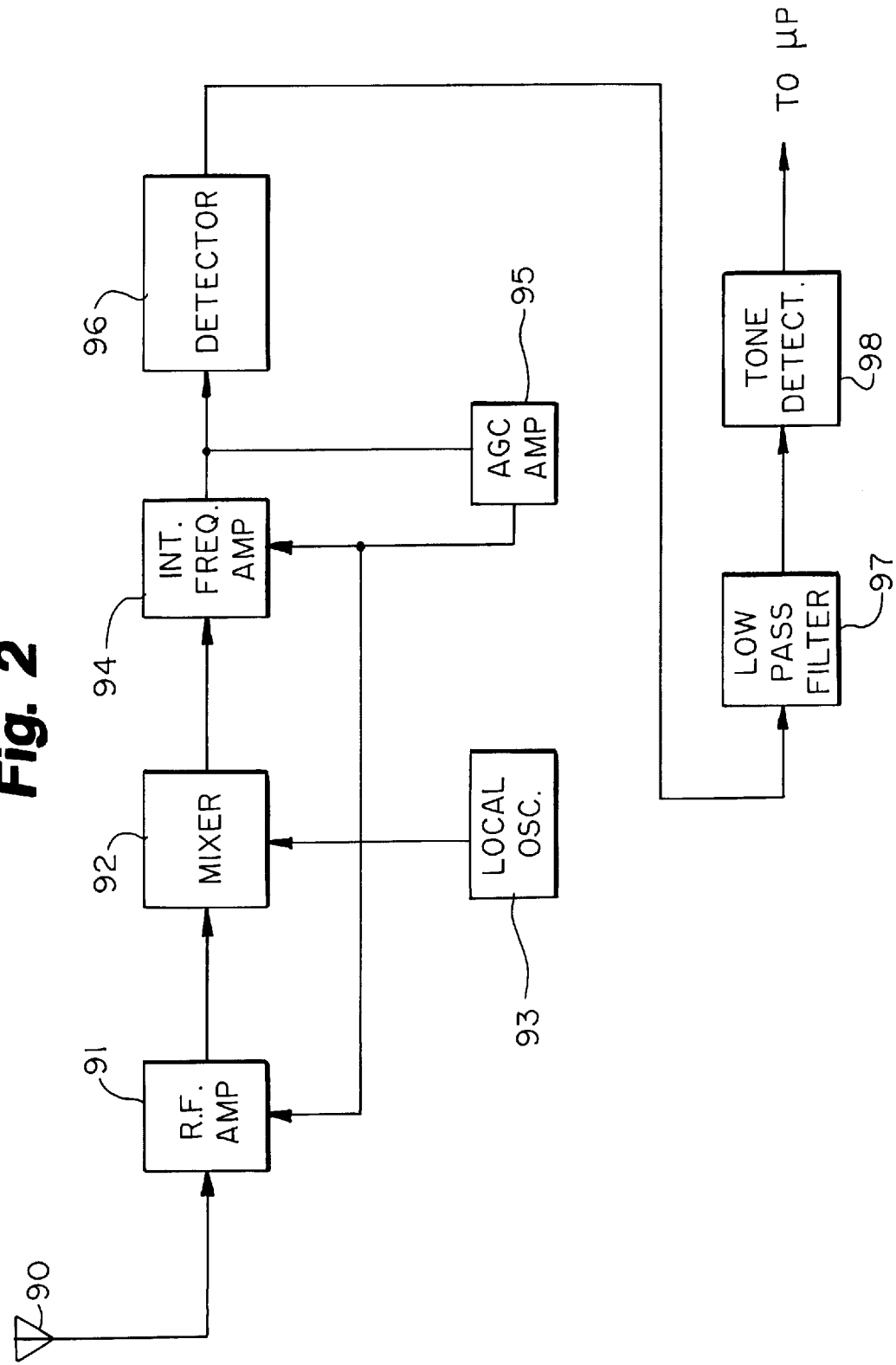

SYNCHRONIZATION METHOD AND APPARATUS FOR ISOLATED CLOCK SYSTEM

FIELD OF THE INVENTION

The present invention relates generally to method and apparatus for synchronizing and processing time data originating from isolated sources. Particularly, the present invention is, preferably, a digital control system for synchronizing time data for clocks using a common reference time determinant. More particularly, the present invention pertains to automated external defibrillators (AEDs) with a digital control system for synchronizing an internal clock with radio broadcasts of standard time.

BACKGROUND OF THE INVENTION

AEDs are used by police officers, paramedics and other first-response emergency medical personnel to resuscitate cardiac arrest patients. As such, AFDs are typically used in responding to a 911 call (or a call to another local emergency number). Upon the receipt of such an emergency call, an emergency medical system (EMS) is usually activated, which then dispatches EMS personnel to the scene. EMS personnel are then responsible for reaching the patient and using the AED to defibrillate the patient. After cardiac stabilization the patient is usually transported to the hospital.

In order to adequately assess the response times and efficiencies of an emergency medical system, it is necessary to track the time between the receipt of the 911 call and the time at which care is first administered to the patient. Typically, the response time is calculated by comparing the time of the 911 call (as recorded on the 911 emergency computer) to the time of the first shock delivery (as recorded on the internal real time clock on the ALD). Unfortunately, it is often difficult to accurately measure this time due to inherent problems of comparing times on two independent clocks. This is especially true as the internal clock in an AED may differ with time relative to the 911 clock. As a result, the response times measured through the AED real time clock often included errors of many minutes. The magnitude of this error is extremely significant in light of studies which indicate that the chances for successful resuscitation diminish approximately ten percent per elapsed response minute. Accordingly, it is evident that there is a need for increased accuracy in measuring response times using AEDs.

SUMMARY OF THE INVENTION

The present invention is a method and apparatus for synchronizing time data which is received from uncoordinated and unrelated sources. More particularly, the preferred embodiment pertains to the provision of an accurate measurement of response times relating to an AED intervention initiated by an emergency medical signal or call.

An embodiment of the present invention, preferably, includes the use of a radio receiver tuned to receive radio broadcasts which carry time signals for Coordinated Universal Time (UTC). The broadcast signals are preferably received by a radio receiver integrated with the AED processor and control system. The time signals are used to set the internal clock of the AED. Similarly, the broadcast signals could be used to set the clock recording the time of an original emergency call.

The present invention therefore provides an accurate measurement of response times based on multi-source clock data. Although the disclosure hereinbelow relates to the preferred embodiment in which an AED internal clock and an internal clock for emergency medical signals are synchronized, the invention is generically applicable to systems where time data from various sources need to be synchronized to measure real time between recorded events.

With these and related features and advantages of the present invention that may become hereinafter apparent, the nature of the invention may be more clearly understood by reference to the following detailed description, the appended claims, and to the drawings herein.

BRIEF DESCRIPTION OF THE DRAWINGS

FIG. 2 is a block diagram of the receiver for amplitude modulated signal such as WWV.

DETAILED DESCRIPTION OF THE PREFERRED EMBODIMENTS

Figure 1B:
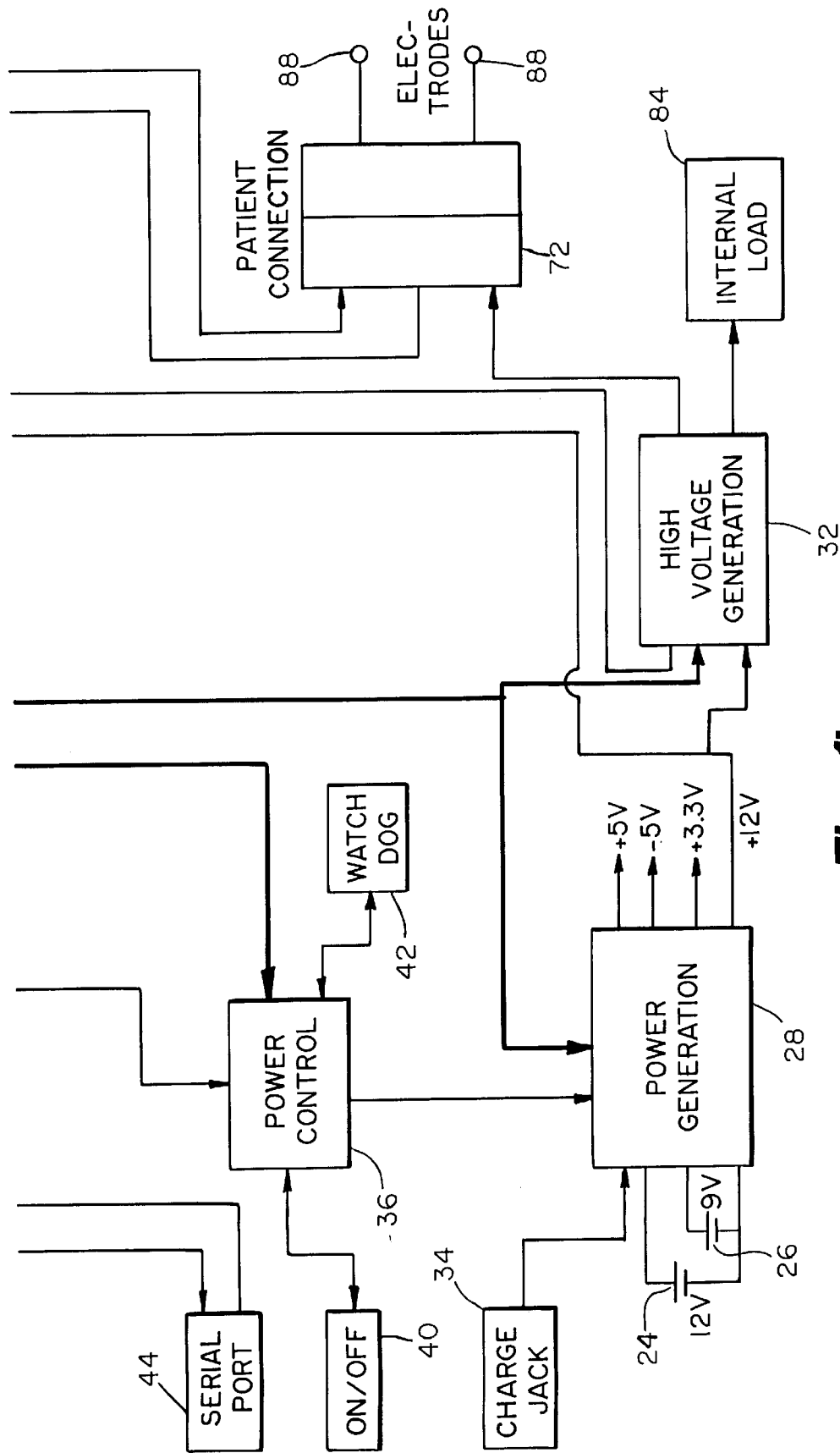
FIG. 1 is a block diagram of the electrical system of the AED.

Referring now to FIG. 1, a block diagram of the electrical system of the AED is shown. The overall operation of the AED is controlled by a digital microprocessor-based control system 10 which includes a processor 12 interfaced to program memory 14, data memory 16, event memory 18 and real time clock 22. The operating program executed by processor 12 is stored in program memory 14. Data memory 16 is used by processor 12 as a scratch pad memory during the execution of the operating program. Electrical power is provided by a rechargeable twelve volt lead-acid cartridge battery 24 and a nine volt battery 26 which are detachably disposed within the battery compartment and connected to power generation circuit 28. Nine volt battery 26 functions as a back-up battery to power components of the electrical system of the AED during the execution of self-tests and to activate maintenance indicators and alarms (as described below) if the twelve volt battery 24 is low on charge.

A high voltage generation circuit 32 is connected to receive the 12 V supply. Charging port at charge jack 34 is coupled to power generation circuit 28, enabling twelve volt battery 24 to be connected to a twelve volt vehicle battery (not shown) or a 120 VAC charger (also not shown) and recharged while mounted within the AED.

Power generation circuit 28 is also connected to power control circuit 36 and processor 12. Power control circuit 36 is connected to lid switch 40, watch dog timer 42, real time clock 22 and processor 12. Data communication port 44 is coupled to processor 12 for two-way serial data transfer using an RS-232 protocol. Rescue switch 46 maintenance indicator 48, rescue switch light 52, resume switch 54 and other indicator lights (not shown) of diagnostic display panel 60, voice circuit 62 and piezoelectric audible alarm 64 are also connected to processor 12. Voice circuit 62 is connected to speaker 66. In response to voice prompt control signals from processor 12, circuit 62 and speaker 66 generate audible voice prompts.

High voltage generation circuit 32 is also connected to and controlled by processor 12. Circuits such as 32 are generally known, and disclosed, for example, in the commonly assigned Persson, et al., U.S. Pat. No. 5,405,361, which is hereby incorporated by reference. In response to charge control signals provided by the processor 12, high voltage generation circuit 32 is operated in a charge mode during which one set of semiconductor switches (not separately shown) cause a plurality of capacitors (also not shown), to be charged in parallel to the 12 V potential supplied by power generation circuit 28. Once charged and in response to discharge, control signals provided by processor 12, high voltage generation circuit 32 is operated in a discharge mode during which the capacitors are discharged in series by another set of semiconductor switches (not separately shown) to produce the high voltage defibrillation pulses. The defibrillation pulses are applied to the patient through electrode connector 72 which is connected to the high voltage generation circuit 32.

The AED electrical system also includes electrocardiogram (ECG) filter and amplifier 74 which is connected between electrode connector 72 and A/D converter 76. The ECG or cardiac rhythm of the patient is processed by filter and amplifier 74 in a conventional manner, and digitized by A/D) converter 76 before being coupled to processor 12.

One of the significant aspects of the present invention includes a radio receiver 78 which is coupled to processor 12 and to antenna 82. As will be discussed hereinbelow, this circuit in conjunction with the electrical system of the AED provides the method and apparatus for synchronizing the internal clock of the AED. Specifically, the radio receiver 78 is tuned to receive standard time broadcasts such as those broadcast by WWV near Ft. Collins, Colo. and by WWVH in Hawaii. These two stations broadcast round-the-clock short-wave broadcasts of time and frequency signals on 1.5, 5, 10, and 15 megahertz. WWV also broadcasts at 20 megahertz. WWVB is a third station which broadcasts standard time signals. WWVB also operates near Fort Collins, Colo., and broadcasts at 60 kilohertz. WWV, WWVH, and WWVB are all operated by the National Institute of Standards and Technology (NIST), an agency of the Technology Administration of the U.S. Department of Commerce.

The broadcasted signals incorporate time signals for Coordinated Universal Time (UTC). This time forms the basis for all civil time and corresponds to local mean time at the Greenwich Observatory in Greenwich, England (Greenwich Mean Time). The time used for standard time broadcast is based on an atomic clock and is corrected by occasionally adding leap seconds to the clock. In addition to including UTC time in both voice and coded form, the broadcasted signals also carry standard carrier frequencies, time intervals and audio tones; information about upcoming storms; and other public service announcements.

Referring now to FIG. 2, a typical block diagram of radio receiver 78 is shown. For purposes of illustration, receiver 78 is considered specifically designed to receive a WWV standard time broadcast or equivalent as discussed hereinabove.

Receiver 78 includes tuned circuit AM aerial 90 which receives 10 MHz or 5 MHz signals from the WWV broadcast. The signal is then passed through radio frequency amplifier 91. A line from automatic gain control amplifier 95 feeds a proportion of the signal passed by intermediate frequency amplifier 94 to radio frequency amplifier 91 to achieve automatic volume control. The signal from radio frequency amplifier 91 is then passed to mixer 92. Mixer 92, in cooperation with local oscillator 93, shifts the signal from radio frequency amplifier 91 to an intermediate frequency. The signal is shifted down in frequency by an amount equal to the frequency of the local oscillator 93. The mixing frequency is generally dependent on the broadcast frequency band because the frequency must be chosen so that intermediate frequency bands are shifted into a distortion free part of the wideband audio. In the preferred embodiment, the exemplary intermediate frequency band is set at about 455 KHz.

The intermediate frequency is then passed through an intermediate frequency amplifier 94. Auto gain control amplifier 95 provides feedback to intermediate frequency amplifier 94 to eliminate distortion of the signal before it is passed on to detector 96. Recovered audio at detector 96 is then passed through pretransmission low pass filter 97 to suppress the low frequency signal generated by mixer 92. Ultimately, the filtered signal is passed through tone detector 98 and is directed to processor 12 in AED control system 10.

Figure 3:
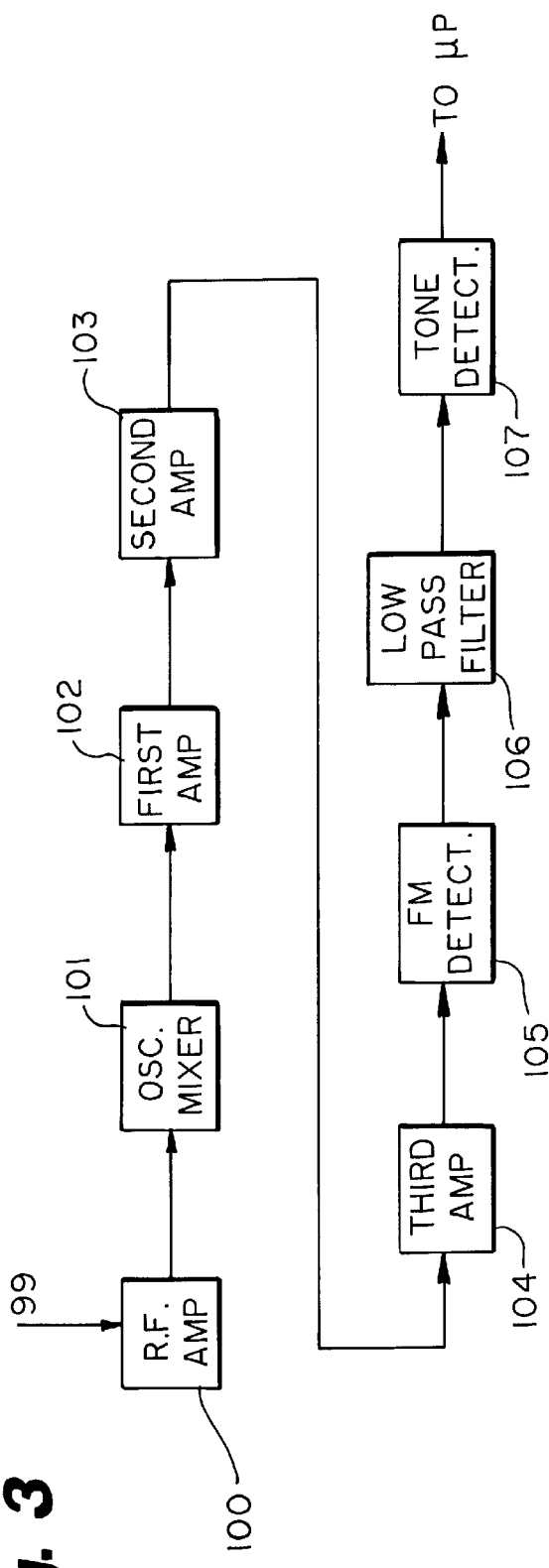
FIG. 3 is a block diagram of the receiver for frequency modulated signal.

FIG. 3 is an alternate embodiment for FM signal reception in which receiver 78 includes an FM aerial 99 transferring signal to radio frequency amplifier 100. The signal is then passed to oscillator and mixer 101 where a desired intermediate frequency is generated. The desired intermediate frequency is transferred to 1st, 2nd and 3rd amplifiers 102, 103 and 104. These series of amplifications provide a highly accurate tuning at the desired frequency. Hereinafter, the signal is passed through low-pass filter 106 where the low frequency bands are suppressed. The filtered signal is then passed through tone detector 107 from where data stream is sent to processor 12 in the AED control system 10.

Processor 12 is able to utilize the radio receiver 78 in order to monitor standard time broadcasts of UTC time. Through procedures well known in the prior art, processor 12 can obtain the current time through the radio receiver 78, and reset real time clock 22 to correspond to the received UTC time.

A periodic self-test is initiated and performed by processor 12 at a predetermined time interval. in the preferred embodiment self-test is executed at least once each day (i.e., every twenty-four hours). During the periodic self-test processor 12 performs all the component check operations. In addition to illuminating the appropriate lights on diagnostic display panel 70, processor 12 switches maintenance indicator 48 to its maintenance required state and activates alarm 64 if faults are identified during the daily self-test.

Processor 12 also initiates and performs a weekly self-test at a predetermined time one day each week. During the weekly self-test processor 12 performs all the component check operations described above that are performed during the periodic self-test. In addition, processor 12 causes high voltage generation circuit 32 to sequentially operate in its charge and discharge modes, with the charge being dumped to the internal load 84. While the high voltage generation circuit 32 is operating in the charge mode, processor 12 monitors the time required to charge the capacitors and the capacitor voltage. A fault is identified if either is out of nominal conditions. Maintenance indicator 20 and alarm 64 are actuated in the manner described above if any faults are identified during the weekly self-test.

As part of the daily self-test, the AED may also reset real time clock 22 according to the standard time received by radio receiver 78, as described above. By operating on a daily basis, this resetting of real time clock 22 will prevent any significant drift in real time clock 22 away from actual local time. This process could also be initiated on a weekly basis during the weekly self-test, or could even be initiated during the one minute CPR cycle during actual use of the AED. The process for updating real time clock 22 generally takes about 45 seconds.

Upon the completion of each periodic, preferably daily and weekly, self-test processor 12 causes a record of the self-test to be stored in event memory 14. Each stored record includes data representative of the date and time of the test and the results of the test. The test results are recorded in the form of a code or other description indicating whether all the functions, components and component status states passed the test, or indicating the nature of any identified faults. In one embodiment, only the records of the ten most recently performed tests are stored in memory 18.

Data representative of the operation of the AED and the monitored cardiac rhythm of the patient are stored in event memory 18 during rescue mode operation. Stored data representative of the operation of AED includes the real time of the occurrence of each of the following events: 1) the placement of electrodes 88 on the patient; 2) the initiation of the cardiac rhythm analysis voice prompt; 3) the initiation of the charging voice prompt; 4) the completion of the charge mode operation of high voltage generation circuit 32; and 5) the actuation of rescue switch 46. The actual time base of the patient's cardiac rhythm is also stored in memory 18.

Figure 4:
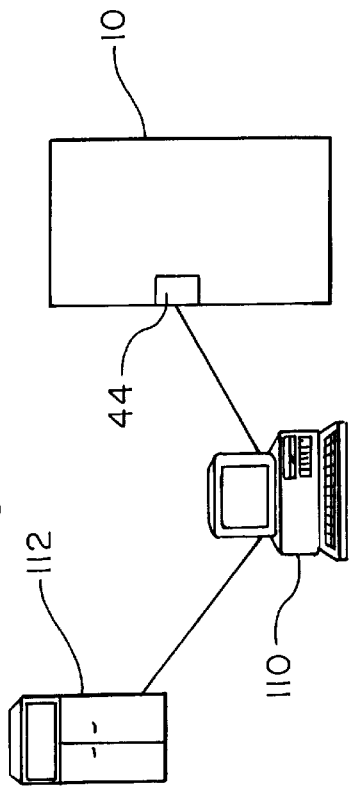
FIG. 4 is a block diagram of the data download system for downloading, data from the AED electrical system of FIG. 1.

Referring now to FIG. 4, a method and apparatus to synchronize clocks is shown. Specifically, a 911 clock is synchronized with an AED internal clock 22 (see also FIG. 1). Generally, the synchronization process is initiated by downloading data stored in the event memory 18 of the AED through the use of a personal computer (PC) 110 interfaced to communications port 44. An emergency phone call control computer 112, which tracks the time of the incoming 911 emergency call, can also be accessed by personal computer 110. A download program running on personal computer 110 coordinates the downloading of information from AED control system 10 and emergency 911 computer 112. The assignee of the present invention is also an assignee of co-pending application entitled Recorded Data Correction Method and Apparatus for Isolated Clock Systems. That invention deals with a computer implemented software method and apparatus for correcting the time difference between the AED internal clock and the 911 computer clock and is hereby incorporated by reference.

The clock on the emergency 911 computer 112 can also be reset to match broadcasts of standard time through radio broadcasts as described above. In addition, the emergency 911 computer 112 could reset its clock using a modem to access the Automated Computer Time Service (ACTS) provided by NIST. This service is through the use of specifically designed software which accesses a clock signal through the modem. The software and the current telephone number of the clock signal can be obtained through the Time and Frequency Division of NIST, 325 Broadway, Boulder, Colo. 80303. Further, the clock can be manually set using a voice telephone. Typically, all computers in a system are set by calling the 911 operator and asking for the 911 time.

It would be clear to one skilled in the art that the personal computer 110 could be one and the same as the emergency phone call computer 112. If this were the case, the personal computer would simply set its own internal clock to coincide with the standard time broadcasts.

Once real time clock 22 of the AED and the clock on emergency 911 computer 112 have both been set to standard time broadcasts, most of the error which stems from comparing the time values of two different clocks has been removed Thus, it is clear that the system described in this application offers considerable advantages and provides a reliable synchronization method and apparatus for isolated time clocks.

Although the present invention has been described with reference to preferred embodiments, those skilled in the art will recognize that changes can be made in form and detail without departing from the context and scope of the claims provided below.

What is claimed is:

1. A method of recreating a historical time sequence in order to monitor and evaluate response time in a life critical cardiac intervention evolution, the intervention being carried out by at least two independent caregivers, the independent caregivers not relying on organizational or technical continuity or compatibility, comprising the steps:

correcting an automated electronic defibrillator (AED) clock by matching a standard time radio broadcast;

time correcting intervention data stored in an AED memory;

downloading time-corrected intervention data stored in the AED memory to a computer;

correcting a clock of an emergency caregiver data storage means by matching a standard time radio broadcast, as needed;

merging the time-corrected AED intervention data and the time-corrected emergency caregiver data in the computer; and recreating a historical time sequence of the intervention by comparing the time-corrected AED intervention data and the time-corrected emergency caregiver data.

2. The method of claim 1 including the step of receiving the standard time radio broadcast by means of a receiver and antenna, the receiver and antenna being integral to the AED.

3. The method of claim 2 including the step of communicating the standard time radio broadcast from the receiver to an AED processor, the AED processor utilizing the standard time radio broadcast to correct the AED clock.

4. The method of claim 3 including the step of filtering a received signal related to a standard time and passing the filtered signal related to a standard time through a tone detector to the AED processor.

5. The method of claim 3 including the step of correcting the AED clock as part of a periodic self test.

6. The method of claim 5 including the step of correcting the AED clock as part of a daily self test.

7. The method of claim 3 including the steps of;

receiving a broadcast signal related to a standard time;

amplifying the received signal;

automatically controlling the volume of the received signal;

shifting the received signal to an intermediate frequency;

amplifying the intermediate frequency signal;

eliminating distortion of the signal;

filtering the signal;

suppressing low frequency bands;

passing the signal through a tone detector; and sending the data stream related to a standard time to the AED processor.

8. The method of claim 1 wherein the intervention data stored in an AED memory includes the time occurrence of intervention events.

9. The method of claim 1 wherein the intervention data stored in an AED memory includes the time occurrence of the following events:

placement of electrodes on the patient;

initiation of a cardiac rhythm analysis voice prompt;

completion of a charge mode operation of a high voltage generation circuit; and actuation of a rescue switch to deliver an energy charge to the patient.

10. The method of claim 1 wherein the emergency caregiver data includes at least the time of reception of a 911 call requesting assistance for a stricken patient.

11. The method of claim 1 wherein the computer is a personal computer.

12. The method of claims 1 wherein the computer is a 911 computer.

\* \* \* \* \*